United States Patent [19]

Stüer et al.

[11] Patent Number: 5,274,098

[45] Date of Patent: Dec. 28, 1993

[54] AMIDINOPHENYLALANINE DERIVATIVES, PROCESS FOR THEIR PREPARATION, THEIR USE AND COMPOSITIONS CONTAINING THEM

[75] Inventors: Werner Stüer, Lahntal; Gerhard Dickneite, Marburg, both of Fed. Rep. of Germany

[73] Assignee: Behringwerke Aktiengesellschaft, Marburg, Fed. Rep. of Germany

[21] Appl. No.: 864,547

[22] Filed: Apr. 7, 1992

[30] Foreign Application Priority Data

Apr. 9, 1991 [DE] Fed. Rep. of Germany ....... 4111394

[51] Int. Cl.$^5$ ................ C07D 211/06; C07D 405/10
[52] U.S. Cl. ......................... 546/226; 546/196; 546/205; 540/200; 540/483; 540/607; 548/540; 564/81
[58] Field of Search ............... 540/200, 483, 607; 546/226, 205, 196; 548/540; 564/81; 514/210, 212, 183, 330, 423, 605, 319, 320

[56] References Cited

U.S. PATENT DOCUMENTS 4,028,380  6/1977  Panneman et al. ............. 546/196

FOREIGN PATENT DOCUMENTS 0236163  9/1987  European Pat. Off. .
0236164  9/1987  European Pat. Off. .
155954   7/1982  German Democratic Rep. .
235866   5/1986  German Democratic Rep. .

OTHER PUBLICATIONS

Selective Inhibition of Thrombin by (2R,4R)-4-Methyl-1-[N$^2$-[(3-methyl-1,2,3,4-tetrahydro-8-quinolinyl)sulfonyl]-L-arginyl(-]-2-piperidinecarboxylic Acid by R. Kikumoto et al., Biochemistry (1984) vol. 23, pp. 85–90.

Comparison of the Anticoagulant and Antithrombotic Effects of Synthetic Thrombin and Factor Xa Inhibitors by J. Hauptmann et al., Thrombosis and Haemostasis 63(2):220–223 (1990).

Pharmacological Characterization of a New Highly Effective Synthetic Thrombin Inhibitor by B. Kaiser et al., Biomed. Biochim. Acta 44 (1985) 7/8, pp. 1201–1210.

Synthese von Na-(Arylsulfonylglycyl)amidinophenylalaninamiden als hochaktive Inhibitoren des Thrombins by G. Wagner et al., Pharmazie 39 (1984) pp. 226–230.

Chemical Abstracts, vol. 110(7): 5094t (1989).
Chemical Abstracts, vol. 110(11): 95774q (1989).
Chemical Abstracts, vol. 111(9): 70596h (1989).

J. Stuerzebecher et al. "Synthetische Inhibitoren der Serinproteinasen," Pharmazie, 42, (1987), pp. 114–121.

D. Horn et al., "Synthese von N α-(8-Chinolonsulfonyl)-4-amidino-phenylalaninamiden Throbininhibitoren," Pharmazie, 40, (1985), pp. 615–616.

Primary Examiner—C. Warren Ivy
Assistant Examiner—Celia Chang
Attorney, Agent, or Firm—Finnegan, Henderson, Farabow, Garrett & Dunner

[57] ABSTRACT

Amidinophenylalanine derivatives, a process for their preparation, their use and pharmaceutical compositions which contain these compounds are described.

13 Claims, No Drawings

AMIDINOPHENYLALANINE DERIVATIVES, PROCESS FOR THEIR PREPARATION, THEIR USE AND COMPOSITIONS CONTAINING THEM

The invention relates to amidinophenylalanine derivatives, a process for their preparation, their use and pharmaceutical compositions which contain these compounds.

As is known, a number of pathophysiological conditions lead to consumption of antithrombin III (AT III), the most important thrombin inhibitor in the plasma. A decrease in AT III leads to an increased risk of thrombosis, as is also known, inter alia, from cases having an inborn deficiency of AT III. A decrease to values below 75% of normal has thromboembolic complications as a consequence. These complications frequently occur in the form of disseminated intravasal clotting after operations and in states of shock. In many cases, life-threatening blood clots occur. For the therapy and prophylaxis of thrombotic diseases, until now anticoagulants having different modes of action have been employed in medicine. For the acute control of a risk of thrombosis, substances such as AT III, heparin and recently also hirudin have been employed. Long-term prophylaxes have been carried out using coumarin and indandione derivatives. However, said anticoagulants are affected by in some cases considerable disadvantages.

Heparin, for example, can only be administered parenterally owing to its polysaccharide structure and its action is also dependent on a functioning antithrombin III level. Coumarins directly counteract protein biosynthesis in that the vitamin K-dependent clotting factors II, VII, IX and X are no longer adequately made available and the clotting potential is thus reduced. From this, a transitory delay in the action results. Known side effects are hemorrhagic skin necroses, nausea and loss of hair.

In contrast, low molecular weight thrombin inhibitors have the advantage that they act directly on thrombin in a cofactor-independent manner by binding directly to the active center and thus, as it were, shutting off the enzyme. Owing to their chemical structure, these substances can be administered orally and display their action immediately.

Amino acid derivatives based on arginine or amidinophenylalanine have achieved particular fame. The first group includes compounds such as D-phenylalanyl-L-prolylarginine aldehyde and (2R,4R)-4-methyl-1-[N2-(3-methyl1,2,3,4-tetrahydro-8-quinolinesulfonyl -L- arginyl]-4-piperidinecarboxylic acid monohydrate ("MD 805"). MD 805 is a competitive specific thrombin inhibitor which is also employed therapeutically. A further known amidinophenylalanine derivative is beta-naphthylsulfonylglycyl-R,S-4-amidinophenylalanyl-piperidide (NAPAP). EP 0,236,163 and EP 0,236,164 describe derivatives of NAPAP. In these derivatives, glycine is replaced by an amino acid of the structure NH-CHR1-COOH, in which R1 is a lower alkyl group, a lower hydroxyalkyl group, a phenyl group or a 4-hydroxyphenyl group. The 4-amidinophenylalanine (Aph) can be N-methylated to give N-methyl-Aph. Additionally, for NAPAP various derivatizations on the arylsulfonyl, "bridging" glycine and on the piperidine ring were described. The most suitable are accordingly alpha- or beta-naphthylsulfonyl groups on the N terminus, against which heteroarylsulfonyl groups such as 8-quinolinesulfonyl are poorer by a power of ten. A disadvantage of natural amino acids as a bridging member between the hydrophobic naphthyl radical and Aph is the enzymatic cleavability of the amide bond to the Aph. This disadvantage particularly has an influence in the case of oral administration. Replacement by another bridging member such as beta-alanine instead of glycine, however, leads to distinct losses of activity with respect to inhibition of thrombin. Even replacement by imino acids such as proline leads to a loss of action.

The aim of the invention was therefore to provide novel compounds based on amidinophenylalanine, which are superior to the known compounds in their antithrombotic activity and have a high enzymatic resistance at the same time as improved tolerability.

This invention therefore relates to compounds of the formula I:

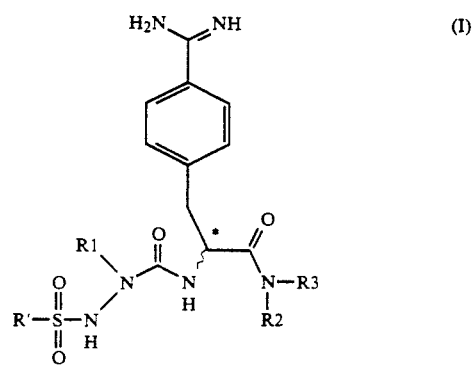

in which

R' is a naphthyl or phenyl group which can be derivatized with one to three alkoxy groups, containing up to three carbon atoms, or with up to five alkyl groups, containing one or two carbon atoms, or a chroman group which can be derivatized with up to five methyl groups, R1 is hydrogen, a lower alkyl group having up to 4 carbon atoms, a hydroxyalkyl group, an aralkyl group having up to 7 carbon atoms i.e. benzyl, or a carboxyalkyl group having up to 4 carbon atoms, R2 and R3 are identical or different and in each case denote an alkyl group having up to 4 carbon atoms, where R2 and R3, together with the nitrogen atom, can form a ring which can be derivatized with a carboxyl group, hydroxyl group or hydroxyalkyl group having up to 3 carbon atoms, and exists in the R or S structure, but preferably in the R structure.

A substantial difference to the known structures is that the atom to which R1 is bonded is a nitrogen atom instead of a carbon atom.

NAPAP has the following structure:

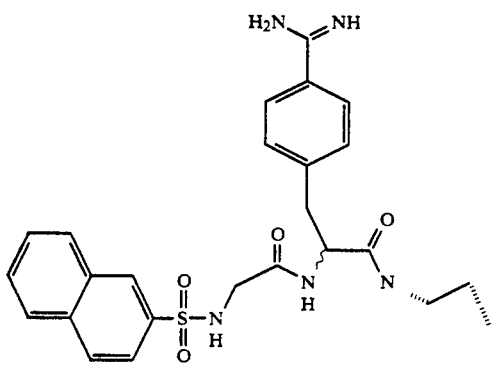

Surprisingly, it was possible to increase the antithrombotic activity considerably by replacement of the glycine in NAPAP by azaamino acid radicals. Azaamino acid radicals are known compounds which can be represented by the following formula:

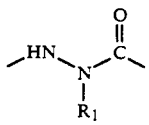

The structural element of the azaamino acids led to structures such as represented above in I.

Surprisingly, β-naphthylsulfonylazaglycyl-D-amidinophenylalanyl-piperidide exceeds the activity of the glycine compound by a factor of 5. The combination of azaamino acids with hydrophobic radicals R' according to formula I leads to compounds having $K_I$ and $IC_{50}$ values in the picomolar range. Moreover, the compounds containing azaamino acids show resistance to enzymatic degradation, so that the compounds according to the invention are characterized by an increased stability in addition to a considerable increase in action.

The compounds according to the invention are prepared by methods known per se as are described, for example, in Houben-Weyl, "Methoden der organischen Chemie" (Methods of Organic Chemistry), volume 15 (1+2), Georg Thieme Verlag Stuttgart, 1974, by Erich Wensch or in Pharmazie 39, 228 (1984).

Preferably, Boc-cyanophenylalanine is first coupled to the "amine component". Amine components employed are preferably cyclic amines such as piperidine, methylpiperidine or hydroxymethylpiperidine. The peptide bond is created by the common standard processes, the reaction preferably being carried out with a carbodiimide in the presence of hydroxybenzotriazole in dimethylformamide or a comparable solvent. After isolation of the N-alpha-protected compound, the protective group, in this case the Boc group, is removed by means of acidolysis. To do this, trifluoroacetic acid, if appropriate in a solvent such as dichloromethane, or HCl in acetic acid, is preferably used for cleavage.

The coupling of the azaamino acid is also carried out by processes known per se such as, for example, the active ester method, in which a protected hydrazine derivative is reacted with chloroformic acid esters to give an active ester. Active esters employed are particularly para-nitrophenyl esters. As a further possibility, activation of the amino group of the cyanophenyl radical to give an isocyanate with subsequent reaction with a hydrazine derivative is possible. The Nβ functions of the hydrazines are blocked during the reactions by protective groups known per se, for which purpose particularly the benzyloxycarbonyl group and very particularly the tertbutyloxycarbonyl group are employed. After acidolytic cleavage of the protective group, an aromatic, heteroaromatic or heterocyclic sulfonyl chloride in a solvent such as tetrahydrofuran, dioxane, dichloromethane or DMF is coupled with the addition of a base such as N-methylmorpholine, triethylamine or diisopropylethylamine. Frequently, however, it proves favorable to couple the sulfonyl chloride derivative to the hydrazine derivative first. The introduction of a protective group can thus be avoided. The conversion of the cyano to the amidino function is carried out by known reaction procedures. Preferably, the corresponding cyanophenylalanine derivative in triethylamine/pyridine is treated over the course of a few days with hydrogen sulfide. The thioamides formed in this way are isolated and converted into the methyl thioimidate compound using a methylating agent such as methyl iodide. By treatment with ammonium compounds such as, for example, ammonium acetate, preferably in methanol as the solvent, the desired amidophenylalanine compound can be obtained.

The compounds are purified by customary methods. Preferably, gel permeation chromatography on materials such as ®Sephadex LH-20 or else ion exchange chromatography on materials such as CM cellulose is used, an acetate buffer being particularly preferably used. The compounds according to the invention are checked for purity by means of thin layer chromatography and HPLC. The identity is examined by means of elemental analysis and NMR.

The inhibitors according to the invention are examined according to various criteria to assess their activity, preferably these are the determination of the Ki value, the $IC_{50}$ value or the partial thromboplastin time (PTT) in vivo and in vitro. The claimed compounds are therefore specific and highly active thrombin inhibitors having a considerable antithrombotic potential which clearly exceeds that of the low molecular weight inhibitors known hitherto.

The invention also relates to diagnostic compositions or therapeutic compositions having antithrombotic action and which contain the inhibitors described, and the use of these compounds as diagnostics or in a process for the preparation of a pharmaceutical having antithrombotic action.

The following examples describe the invention in greater detail:

EXAMPLE 1

Beta-naphthylsulfonyl-azaglycyl-D-p-amidinophenylalanylpiperidide

1. Boc-D-p-cyanophenylalanyl-piperidide 50 g (255 mmol) of p-cyanobenzyl bromide, 55 g (255 mmol) of diethyl acetamidomalonate and 2 g of potassium iodide were heated to boiling in 250 ml of abs. dioxane. A freshly prepared solution of 6 g (260 mmol) of sodium in ethanol was added dropwise to this mixture in the course of 3 hours. After boiling under reflux for a further 3 hours, the mixture was cooled to 80 degrees and 170 ml of sodium hydroxide solution were added in the course of 3 hours. The mixtures was heated to 95 degrees for 4 hours. After cooling, it was adjusted to pH 1 with 6N HCl and the dioxane was evaporated.

Any precipitate deposited was filtered off. The mixture was adjusted to pH 9 with sodium hydroxide solution and extracted twice with ethyl acetate. The aqueous phase was again adjusted to pH 1 with hydrochloric acid, whereupon N-acetylcyanophenylalanine crystallized out. The crystals were collected, washed several times with water and dried in a high vacuum.

Yield: 47 g (79.2% of theory).

Purity testing: TLC Rf 0.5 (chloroform 50/methanol 10/glacial acetic acid 2.5 parts by volume).

24 g of this product were dissolved in 3 liters of water by addition of 3N sodium hydroxide solution and the pH was adjusted to 6–6.5. 500 mg of acylase were added to this mixture and it was incubated at 37 degrees for 4 days. After this, the solution was freed of acylase by ultrafiltration and then concentrated to a volume of 1 liter. After adjustment to pH 1, the mixture was extracted several times with ethyl acetate. The organic phase was washed with a little conc. sodium chloride solution and dried over sodium sulfate, and the solvent was evaporated. 8.2 g of N-acetyl-D-cyanophenylalanine were obtained (82% of theory). 22 ml of glacial acetic acid and 4.3 ml of conc. hydrochloric acid contained in 40 ml of water were added to 8 g of this compound and the mixture was heated to boiling for 24 hours. After evaporation of the cleavage solution and subsequent entrainment of adhering traces of acid with methanol, the product was dissolved and reprecipitated from methanol/diethyl ether.

Yield: 6.6 g (85% of theory).

5 g of D-cyanophenylalanine hydrochloride were dissolved in 14 ml of water with the addition of 7.5 ml of diisopropylethylamine. A solution of 6 g of tert-butyloxycarbonyl-oximino-2-phenylacetonitrile in 17 ml of dioxane was added to this mixture and it was stirred overnight. 40 ml of water and 50 ml of ethyl acetate were added. The water phase was separated off and the organic phase was extracted again with 1M potassium hydrogen carbonate. The combined aqueous phases were washed again with 10 ml of diethyl ether and then adjusted to pH 3 with hydrochloric acid. Extraction was carried out 3 times using ethyl acetate, and the organic phase was washed with sodium chloride solution and dried over sodium sulfate. After were obtained evaporation of the solvent, 5.6 g (78%) of Boc-D-cyanophenylalanine were obtained. 3.26 g (10 mmol) of Boc-D-cyanophenylalanine, 1.49 g 11 mmol) of HOBt and 2.42 g (12 mmol) of DCCI were dissolved in 50 ml of DMF and the solution was stirred for 1 hour. 1 ml of piperidine was added and the mixture was stirred overnight. Precipitated dicyclohexylurea was filtered off, the DMF was removed by distillation and the residue was taken up in ethyl acetate. The solution was washed 3 times with potassium hydrogen carbonate, 3 times with 1M potassium hydrogen sulfate and 3 times with satd. sodium chloride solution. After drying the organic phase using sodium sulfate and removing the solvent by distillation, 3.16 g (80%) of Boc-D-cyanophenylalanyl-piperidine idide were obtained Purity checking: TLC Rf =0.27 (chloroform).

2. D-Cyanophenylalanyl-piperidine hydrochloride 3 g of the Boc-protected compound were dissolved in 50 ml of 1.2N HCl in glacial acetic acid and the mixture was stirred at room temperature for 30 min. The cleavage reagent was removed by distillation in vacuo, the solvent was subsequently entrained with toluene and the residue was triturated with a little diethyl ether. The crystals were collected and dried in vacuo.

Yield: 2.2 g.

3. Boc-Azaglycyl-D-cyanophenylalanyl-piperidide 2.08 g (7 mmol) of Boc-azaglycine-para-nitrophenyl ester and 2.06 g (7 mmol) of cyanophenylalanyl-piperidide were dissolved in 50 ml of DMF. After addition of 2.4 ml (14 mmol) of diisopropylethylamine, the mixture was stirred at room temperature in the dark for 1 day. The solvent was removed by distillation in vacuo, the residue was taken up in ethyl acetate and the solution was washed 3 times with 1M potassium hydrogen sulfate solution, 3 times with potassium hydrogen carbonate solution and twice with conc. sodium chloride solution. The organic phase was dried over sodium sulfate and the solvent was evaporated. The residue was stirred with diisopropyl ether, and the crystals were collected and dried. 2.29 g of Boc-azaglycyl-D-cyanophenylalanyl-piperidide were obtained.

4. Beta-naphthylsulfonyl-azaglycyl-D-cyanophenylalanylpiperidide 2.08 g (5 mmol) of Boc-azaglycyl-D-cyanophenylalanylpiperidide were dissolved in 50 ml of 1.2N HCl in glacial acetic acid and the mixture was stirred at room temperature for 30 min. After evaporation of the cleavage reagent and subsequent entrainment with toluene in vacuo, the residue was triturated with ether and the crystals were collected. The crystals were dissolved in 50 ml of dichloromethane with the addition of 1.7 ml (10 mmol) of diisopropylethylamine. 1.134 g of $\beta$-naphthylsulfonyl chloride were added to this mixture and it was stirred overnight at room temperature. The solvent was removed by distillation, the residue was taken up in ethyl acetate and the solution was washed 3 times with 1M potassium hydrogen sulfate solution, 3 times with potassium hydrogen carbonate solution and twice with conc. sodium chloride solution. The organic phase was dried over sodium sulfate and the solvent was evaporated. 1.75 g of $\beta$-naphthylsulfonyl-azaglycyl-D-cyanophenylalanylpiperidide were obtained.

5. Beta-naphthylsulfonyl-azaglycyl-D-amidinophenylalanylpiperidide 1 g of the compound obtained in 4. was dissolved in 30 ml of dry pyridine and, after addition of 1 ml of triethylamine, hydrogen sulfide gas was passed in for 3 hours. After allowing to stand at room temperature for 3 days, the solution was poured onto a mixture of 100 g of ice and 50 ml of conc. hydrochloric acid. The precipitate was filtered with suction and washed with water. After drying, the thioamide was taken up in 50 ml of acetone and the solution was treated with 1.5 ml of methyl iodide. It was boiled under reflux for 30 minutes. After cooling, precipitation was carried out using diethyl ether. The precipitate was dissolved in dichloromethane and washed twice with water. After drying the organic phase over sodium sulfate and removing the solvent, the residue was taken up in 30 ml of dry methanol and 200 mg of ammonium acetate were added. The mixture was heated to 60 degrees for 3 hours. The solvent was evaporated in vacuo. The product was subjected to a chromatographic purification on ®Sephadex LH-20 in methanol.

Yield: 590 mg

Purity checking: melting point 182° C. TLC: Rf =0.48 (chloroform 50/methanol 10/glacial acetic acid 2.5 volumes.

Identity checking: Molecular weight determination (fast atom bombardment) M H+523.

EXAMPLE 2

Pmc-Azaglycyl-D-p-amidinophenylalanylpiperidide

The steps 1.-3. are identical to the previous example

4. Pmc-Azaglycyl-D-cyanophenylalaninepiperidide 1.67 g (4 mmol) of Boc-azaglycyl-D-cyanophenylalanylpiperidide were dissolved in 50 ml of 1.2 N HCl in glacial acetic acid and the mixture was stirred at room temperature for 30 min. After evaporation of the cleavage agent and subsequent entrainment with toluene in vacuo, the residue was triturated with ether and the crystals were collected. The crystals were dissolved in 50 ml of dichloromethane with the addition of 1.36 ml (8 mmol) of diisopropylethylamine. 1.35 g of Pmc chloride were added to this mixture and it was stirred overnight at room temperature. The solvent was removed by distillation, the residue was taken up in ethyl acetate and the solution was washed 3 times with 1M potassium hydrogen sulfate solution, 3 times with potassium hydrogen carbonate solution and twice with conc. sodium chloride solution. The organic phase was dried over sodium sulfate and the solvent was evaporated. 1.95 g of Pmc-azaglycyl-D-cyanophenylalanylpiperidide were obtained.

5. Pmc-Azaglycyl-D-amidinophenylalanylpiperidide 1.5 g of the compound obtained in 4. were dissolved in 30 ml of dry pyridine and, after addition of 1 ml of triethylamine, hydrogen sulfide gas was passed in for 3 hours. After allowing to stand at room temperature for 3 days, the solution was poured onto a mixture of 100 g of ice and 50 ml of conc. hydrochloric acid. The precipitate was filtered with suction and washed with water. After drying, the thioamide was taken up in 50 ml of acetone and treated with 1.5 ml of methyl iodide. The mixture was boiled under reflux for 30 minutes. After cooling, precipitation was carried out using diethyl ether. The precipitate was dissolved in dichloromethane and washed twice with water. After drying the organic phase over sodium sulfate and removing the solvent, the residue was taken up in 30 ml of dry methanol and 300 mg of ammonium acetate were added. The mixture was heated to 60 degrees for 3 hours. The solvent was evaporated in vacuo. The product was subjected to a chromatographic purification on ®Sephadex LH-20 in methanol. Yield: 990 mg.

Purity checking: melting point 149°-155° C. (sintering, acetate salt.

TLC: Rf = 0.52 (chloroform 50/methanol 10/glacial acetic acid 2.5 volumes).

Determination of the IC$_{50}$ value of the thrombin inhibition:

The compounds were incubated with human thrombin in 0.1M tris-HCl buffer/0.15 M NaCl pH 8.2 in increasing concentrations. After one hour, the enzymatic reaction was begun by the addition of the substrate Chromozym®TH (Tos-Gly-Pro-Arg-pNA, $5 \times 10^{-5}$ M/l) The release of pNA was measured after one hour as the increase in the optical density at 405 nm in a photometer. The concentration of inhibitor which caused a 50% inhibition in enzyme activity was designated at the IC$_{50}$(100% corresponds to the non-inhibited enzyme reaction).

Determination of the K$_I$ value for thrombin:

The K$_I$ values for the compounds investigated were determined using the abovementioned thrombin solution. To do this, thrombin was incubated with a concentration of inhibitor which approximately corresponded to the IC$_{50}$ value determined in the abovementioned test. The reaction was begun with various concentrations of the substrate Chromozym TH ($0.7-45 \times 10^{-5}$ mol/l). The type of inhibition and the K$_I$ value were determined by the method described by Lineweaver and Burk (J. Amer. Chem. Soc., 56, 658-666, 1934).

TABLE 1

| Compound | Thrombin inhibition | |
|---|---|---|
| | IC$_{50}$ (mol/l) | K$_I$ (mol/l) |
| Pmc—Gly—Aph—Pip | $1.4 \times 10^{-9}$ | $1.3 \times 10^{-9}$ |
| Nas—AGly—Aph—Pip | $1.3 \times 10^{-9}$ | $2.6 \times 10^{-9}$ |
| Pmc—AGly—Aph—Pip | $1.6 \times 10^{-12}$ | $9.2 \times 10^{-11}$ |
| NAPAP | $2.8 \times 10^{-9}$ | $1.4 \times 10^{-9}$ |

Abbreviations
Boc  tert-butyloxycarbonyl
TLC  thin layer chromatography
Rf   retention factor
HOBt hydroxybenzotriazole
DCCI dicylohexylcarbodiimide
DMF  dimethylformamide
Pmc  2,2,5,7,8-pentamethylchroman-6-sulfonyl.

We claim:

1. A compound of the structure I

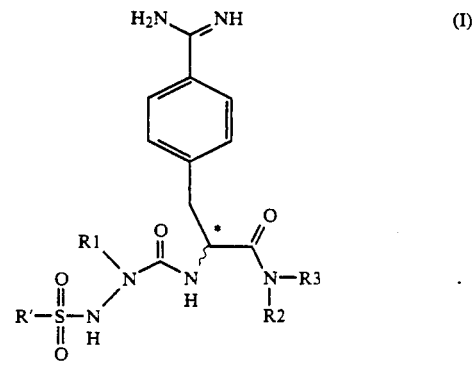

in which

R' is a naphthyl or phenyl group which can be optionally substituted with one to three alkoxy groups, containing up to three carbon atoms, or with up to five alkyl groups, containing one or two carbon atoms, or a chroman group which can be optionally substituted with up to five methyl groups, R1 is hydrogen, a lower alkyl group having up to 4 carbon atoms optionally substituted with a hydroxy group, a benzyl group, carboxyalkyl group having up to 4carbon atoms, R2 and R3 are identical or different and in each case denote an alkyl group having up to 4 carbon atoms, or R2 and R3, together with the nitrogen atom, can form a piperidine ring which can be optionally substituted with a carboxyl group, hydroxyl group or hydroxyalkyl group having up to 3 carbon atoms, and exists in the R or structure.

2. A compound as claimed in claim 1, in which R' is β-naphthyl, R1 is hydrogen and R2 and R3 are together piperidine.

3. A compound as claimed in claim 1, in which R' is 2,2,5,7,8-pentamethylchroman, R1 is hydrogen and R2 and R3 are together piperidine.

4. A compound as claimed in claim 1, in which R' is β-naphthyl, R1 is —CH$_2$-COOH and R2 and R3 are together piperidine.

5. A compound as claimed in claim 1, in which R' is β-naphthyl, R1 is methyl and R2 and R3 are together piperidine.

6. A compound as claimed in claim 1, in which R' is 6,7-dimethoxy-β-naphthyl, R1 is H and R2 and R3 are together piperidine.

7. A compound as claimed in claim 1, in which R' is 5-methoxy-alpha-naphthyl, R1 is methyl and R2 and R3 are together piperidine.

8. A compound as claimed in claim 1, in which R, is β-naphthyl, R1 is H and R2 and R3 are together 3-piperidine.

9. A compound as claimed in claim 1, in which R' is 5,6,7,8-tetrahydro-β-naphthyl, R1 is $CH_2$-COOH and R2 and R3 are together piperidine.

10. A compound as claimed in claim 1, in which R' is methoxytriphenylmethyl.

11. A compound as claimed in claim 1, in which R' is pentamethylphenyl, R1 is H and R2 and R3 are together piperidine.

12. A compound as claimed in claim 1, in which * is in the R structure.

13. A compound as claimed in claim 10, in which R' is 4-methoxy-2,3,6-trimethylphenyl.

* * * * *

UNITED STATES PATENT AND TRADEMARK OFFICE
CERTIFICATE OF CORRECTION

PATENT NO. : 5,274,098
DATED : December 28, 1993
INVENTOR(S) : Werner Stuber et al.

It is certified that error appears in the above-indentified patent and that said Letters Patent is hereby corrected as shown below:

On the title page: Item [75]

first inventor change "Werner Stuer" to --Werner Stüber--.

Claim 1, column 8, line 50, after "benzyl group," insert --or a--.

Claim 1, column 8, line 51, change "4carbon" to --4 carbon--.

Claim 1, column 8, line 58, insert --S-- after "R or".

Claim 8, column 9, line 11, change "R," to --R'--.

Signed and Sealed this

Twenty-sixth Day of July, 1994

Attest:

BRUCE LEHMAN

*Attesting Officer*  *Commissioner of Patents and Trademarks*